United States Patent [19]
Klein et al.

[11] Patent Number: 4,675,178

[45] Date of Patent: Jun. 23, 1987

[54] USE OF CATIONIC POLYMERS (POLYDIMETHYLDIALKYL AMMONIUM CHLORIDE-ACRYLAMIDE COPOLYMERS AND DIMETHYLDIALKYL AMMONIUM CHLORIDE) TO INCREASE DEPOSITION AND/OR RETENTION OF ACTIVE AGENT (S) OF DEODORANT FORMULATIONS ON SURFACES

[75] Inventors: William L. Klein, Nutley; Arthur R. Sykes, East Windsor, both of N.J.

[73] Assignee: Calgon Corporation, Pittsburgh, Pa.

[21] Appl. No.: 729,518

[22] Filed: May 2, 1985

[51] Int. Cl.$^4$ .................. A61K 7/32; A61K 7/36; A61K 7/38

[52] U.S. Cl. ...................... 424/65; 424/66; 424/67; 424/68

[58] Field of Search .............. 424/65, 66, 67, 68

[56] References Cited

U.S. PATENT DOCUMENTS

| | | | |
|---|---|---|---|
| 2,674,580 | 4/1954 | Henkin | 424/70 UX |
| 3,769,398 | 10/1973 | Hewitt | 424/70 |
| 4,329,335 | 11/1982 | Su et al. | 424/70 |
| 4,348,380 | 9/1982 | Jacquet et al. | 424/65 |

FOREIGN PATENT DOCUMENTS

| | | | |
|---|---|---|---|
| 1157777 | 11/1983 | Canada | 424/65 |
| 055857 | 12/1981 | European Pat. Off. | 424/60 |
| 074819 | 9/1982 | European Pat. Off. | 424/70 |
| 0137173 | 4/1985 | European Pat. Off. | 424/65 |
| 2453139 | 5/1975 | Fed. Rep. of Germany | 424/65 |
| 1344224 | 10/1963 | France | 424/65 |

*Primary Examiner*—Dale R. Ore
*Attorney, Agent, or Firm*—W. C. Mitchell; M. Polk; M. C. Sudol

[57] ABSTRACT

The invention relates to stable deodorant compositions comprising at least one antimicrobial agent and polydimethyldialkyl ammonium chloride-acrylamide copolymers or dimethyldialkyl ammonium chloride cationic polymer which serve to enhance the residual efficacy of said agent on a surface.

5 Claims, No Drawings

USE OF CATIONIC POLYMERS (POLYDIMETHYLDIALKYL AMMONIUM CHLORIDE-ACRYLAMIDE COPOLYMERS AND DIMETHYLDIALKYL AMMONIUM CHLORIDE) TO INCREASE DEPOSITION AND/OR RETENTION OF ACTIVE AGENT (S) OF DEODORANT FORMULATIONS ON SURFACES

BACKGROUND OF THE INVENTION

The invention relates to stable deodorant compositions comprising at least one antimicrobial agent and poly-dimethyldialkyl ammonium chloride-acrylamide copolymers (DMDAAC/AM) or dimethyldialkyl ammonium chloride cationic polymer (DMDAAC) which serve to enhance the residual efficacy of said agent on a surface. Also, disclosed herein are methods of administering said stable and effective compositions of the invention.

DESCRIPTION OF THE PRIOR ART

Numerous references disclose cosmetic and personal use detergent compositions such as shampoos, anti-dandruff rinse conditioner and etc., containing anionic and/or cationic polymers, an active agent, surfactants, emollients, and other additives and preservatives commonly employed in the industry. While none of said references employ the specific cationic polymers without surfactants, pertinent references which disclose cosmetic and personal use detergent formulations containing either or both anionic and cationic polymers are discussed below:

1. U.S. Pat. No. 3,761,417 is directed to detergent compositions containing particle deposition enhancing agents. More specifically, the reference discloses detergent and personal use toilet detergent bars containing water-insoluble particles such as antimicrobial agents, organic surfactants and cationic polymers. Surfactants are an essential ingredient of the compositions. DMDAAC is specifically mentioned as a possible cationic polymer.

2. U.S. Pat. No. 3,769,398 discloses non-anionic hair shampoo formulations containing an active ingredient (detergent such as betaines, sulfobetaines, amine oxides and mixtures thereof), a water-soluble polymer (polyethylenimine-ethylene oxide or propylene oride) and propoxylated polyethylenimines.

3. U.S. Pat. No. 4,329,335 describes an amphoteric-nonionic anti-dandruff shampoo containing an active agent (1-imidazalyl-1-(4-chlorophenoxy)-3,3-dimethylbutan-2-one), and amphoteric surfactants, polyoxyethylene hexitan mono or higher fatty acid ester, tertiary amine oxide, fatty acid mono- or di-ethanolamide and optionally a polymerized quarternized ammonium compound. DMDAAC is specifically disclosed as a preferred polymerized quaternized ammonium compound.

4. Published European Patent Application No. 74,819 discloses an anti-dandruff cream rinse conditioner containing zinc pyrithione, homopolymers of DMDAAC or copolymer of DMDAAC-acrylamide, glucan or guar gum and hydroxyethylcellulose.

5. Published European Patent Application No. 55,857 teaches preparation of topically applied compositions comprising ultraviolet light-absorbing materials and film-forming polymers which exhibit enhanced protection from erythema-causing radiation.

SUMMARY OF THE INVENTION

In accordance with this invention, it is found that stable and effective deodorant compositions can be prepared comprising at least one antimicrobial agent, a cationic polymer (poly-dimethyldialkyl ammonium chloride-acrylamide copolymers or dimethyldialkyl ammonium chloride) wherein said polymer enhances the residual efficacy of said antimicrobial agent on the intended surface.

Accordingly, it is an object of this invention to enhance the biological activity of antimicrobial agents by formulation with a cationic polymer.

It is an object of this invention to provide a formulation comprising a new dosage form (lower level) of the active agent.

Another object of this invention is to provide a formulation at such concentration level which will avoid possible future side effects.

Still another object of this invention is to provide a formulation which combines enhanced deodorant activity with skin/hair conditioning benefits.

Other objects, features and advantages of the invention will be apparent to those skilled in the art from the detailed description of the invention which follows.

All of the foregoing objects are readily attained by providing a method and formulation wherein the deposition and/or retention of the antimicrobial agent is enhanced. The method comprises the steps of preparing a formulation suitable for topical application and a formulation comprising an effective amount of the antimicrobial agent, a selective cationic polymer and optionally an anti-perspirant and commonly employed cosmetically acceptable excipients such as buffering and/or preservative agents; the cationic polymer being present in an amount sufficient to be effective in enhancing the rate of deposition and/or retention of the antimicrobial agent on the intended surfaces. Representative surface areas are the skin and hair of the body.

DETAILED DESCRIPTION OF THE INVENTION

The invention generally comprises the steps of preparing formulations capable of being topically administered wherein said formulations comprises an effective amount of an antimicrobial agent, a cationic polymer (poly-dimethyldialkyl ammonium chloride-acrylamide copolymer or dimethyldialkyl ammonium chloride) and optionally an anti-perspirant and cosmetically acceptable excipients such as buffers and/or preservatives. The polymer being present in an amount sufficient to enhance deposition and/or retention of the antimicrobial agent to the intended surface. The formulation is achieved by mixing the polymer with de-ionized water with agitation, adding an emulsifier with continued agitation, heating to a temperature ranging from 65° to 90° C. (preferably at 75° to 80°) until a solution is obtained, and continuing agitation while adding the antimicrobial agents, followed by preservatives, thickening agents, buffers, dyes and/or fragrances, and optionally an antiperspirant agent and ultimately adjusting the formulation by adding the remainder of de-ionized water while maintaining the temperature range.

The amount of the antimicrobial agent varies over a wide range and depends on the specific agent employed. Generally, the antimicrobial effective amount would be considerably less than that amount known in the art to obtain the desired results. Specifically, the amount of antimicrobial agent used in the formulations herein constitutes from 0.01% to 5% (preferably 1% to 2%) of the total formulation weight.

Generally, the amount of polymer employed in the practice of the invention ranges from 0.01% to 12% polymer (preferably 1% to 3%), by weight of the formulation. The remaining portion of the total composition contains the antimicrobial agent and conventional acceptable excipients.

Examples of copolymers of dimethyldiallyl ammonium chloride (DMDAAC) and acrylamide, are Merquat ® S and Merquat ® 550 manufactured by Calgon Corporation. The preferred product is Merquat ® S. Merguat ® 550 and S copolymers have an intrinsic viscosity of 4.2±0.2 and contain about 50 percent by weight, DMDAAC and 50 percent, by weight, acrylamide. Although any ratio of DMDAAC and acrylamide will work, the preferred ratio is 10 to 75 percent, more preferably 25 to 75 percent, by weight, DMDAAC to 25 to 90 percent, more preferably 25 to 75 percent, by weight, acrylamide. Homopolymers of poly(DMDAAC) employed in the invention have a molecular weight ranging from 20,000 to 2,500,000, preferably from 200,000 to 300,000 and an intrinsic viscosity of 0.1 to 2.5, preferably from 0.7–0.9. The preferred polymers are the copolymers of DMDAAC-/AM.

Representative antimicrobial agents employed in the practice of the invention are trichlocarban (3,4,4'-trichloro carbanilide), triclosan (2,4,4'-Trichloro-2'-hydroxy diphenyl ether), benzalkonium chloride, zinc phenosulfonate, zinc ricinoleate and the like.

Representative anti-perspirants within the scope of the invention are aluminum zirconium complex, aluminum chlorohydrate, aluminum chlorohydrex P.G. and the like.

Representative emollients, humectants and moisturizing agents within the scope of the invention are $C_{12}$–$C_{15}$ alcohol benzoates, sorbitol, glycerin, propylene glycol (peg), lanolin, vegetable oils, mineral oils, isopropyl myristate, aloe vera, jojoba oil and the like.

Other cosmetically acceptable excipients that the formulation may contain are thickening agents, buffering agents and preservatives. Suitable water soluble preservatives are sodium bisulfite, sodium thiosulfate, ascorbate, benzalkonium chloride, glydant chlorobutanol, thimerosal, phenylmercuric borate, Dowicil 200 parabens, Tektamer 38(1,2-dibromo-2,4-dicyanobutane), benzyl alcohol, phenylethanol and the like. Suitable thickening agents are Cab-O-Sil M5 made by Cabot Corporation, sodium stearate, magnesium aluminum silicate, hydroxyethyl cellulose and the like. These agents may be present in amounts of from 0.05 to 50% by weight and preferably 1 to 5%. Suitable water soluble buffering agents are alkali or alkali earth carbonates, phosphates, bicarbonates, citrates, borates, acetates, acid anhydrides, succinates and the like, such as sodium phosphate, citrate, borate, acetate, bicarbonate and carbonate. These agents may be present in amounts sufficient to maintain some optimum pH of the system in the range 2 to 9. As such the buffering agent can be as much as 20% on a weight to weight basis of the total composition.

Studies were conducted on the degree of inhibition of antimicrobial activity of deodorants of pig skin with and without a polymer. The organisms tested were mixed innoculum, staphylococcus aureus and escherichia coli using a control which contained no polymer (Example 1) and Merquat 100 and Merquat S as polymers are detailed in Example 2 and 3, respectively. The results are shown in Table I below:

TABLE I

| ANTIMICROBIAL ACTIVITY OF DEODORANTS ON PIG SKIN | | | | |
|---|---|---|---|---|
| | Zone of Inhibition Diameter (in MM*) | | | |
| Test Organism | Control (Example 1) | Merquat 100 (Example 2) | Merquat S (Example 3) | No Treatment |
| mixed innocular | 10.0 | 13.3 | 14.6 | 0 |
| *Staphylococcus aureus* | 27.3 | 30.3 | 35.3 | 0 |
| *Escherichia coli* | 18.3 | 22.6 | 25 | 0 |

*millimeter
A zone of inhibition of growth of the test organism under and surrounding the discs shows that the compound being tested is microbiologically active.
A zero value indicates microbial growth under the disc and no microbiological activity against that test organism.
*These numbers indicate the average of triplicate results.

As noted from Table I, deodorant samples containing Merquat demonstrate better activity than deodorant without Merquat. The enhanced microbiological activity of the deodorant formulation in the presence of the polymer may be due to improved substantivity, retention on skin surface, or improved diffusion of the deodorant's active ingredient.

The following examples illustrate the preparation of various deodorant formulations of the invention. The Examples should be construed as illustrations rather than limitations thereof.

EXAMPLE 1

| | Stick Deodorant Control Formulation* | | |
|---|---|---|---|
| NO. | PHASE | INGREDIENT | % BY WEIGHT |
| 1 | A | deionized water | 14.00 |
| 2 | A | propylene glycol | 74.80 |
| 3 | B | Cab-O-Sil M5 | 2.00 |
| 4 | C | triclosan | 0.20 |
| 5 | D | sodium stearate | 8.50 |
| 6 | E | fragrance | 0.50 |
| | | g.s. | 100.00 |

*Without polymer

With rapid agitation, phase A ingredients were throughly mixed with phase B and the mixture heated to 80° C. while adding phase C. When dissolved, phases D and E were successively added, agitated until dissolved and q.s. to 100%. The resulting mixture was then poured into the suitable containers for personal care application. (Note: Maintain 80° C. temperature while making additions.)

EXAMPLE 2

Stick Deodorant

| NO. | PHASE | INGREDIENT | % BY WEIGHT |
|---|---|---|---|
| 1 | A | deionized water | 14.00 |
| 2 | A | propylene glycol | 72.80 |
| 3 | B | Cab-O-Sil M5 | 2.00 |
| 4 | C | triclosan | 0.20 |
| 5 | D | sodium stearate | 8.50 |
| 6 | E | fragrance | 0.50 |
| 7 | F | Merquat 100 | 2.00 |
|  |  | q.s. | 100.00 |

The reaction conditions and procedure of Example 1 was followed except that "Merquat 100" was substituted for "Merquat S" to obtain the corresponding product.

EXAMPLE 3

Stick Deodorant

| NO. | PHASE | INGREDIENT | % BY WEIGHT |
|---|---|---|---|
| 1 | A | deionized water | 14.00 |
| 2 | A | propylene glycol | 71.80 |
| 3 | B | Cab-O-Sil M5 | 2.00 |
| 4 | C | triclosan | 0.20 |
| 5 | D | sodium stearate | 8.50 |
| 6 | E | fragrance | 0.50 |
| 7 | F | Merquat S | 3.00 |
|  |  | q.s. | 100.00 |

With rapid agitation, phase A ingredients, were throughly mixed with phase B and the resulting mixture heated to 80° C. while adding phase C. When dissolved, phases D and E were successively added and agitated until dissolved. With continued agitation, phase F was added to the mixture and q.s. to 100%. The resulting mixture was then poured into the suitable containers for personal care application. (Note: Maintain 80° C. temperature while making additions).

Following the above reaction conditions and procedure, except that when trichlocarban, benzalkonium chloride, zinc phenosulfonate or benzalkonium chloride is substituted for triclosan, there is obtained the corresponding stick deodorant formulation.

EXAMPLE 4

Roll-on Deodorant

| NO. | PHASE | INGREDIENT | % BY WEIGHT |
|---|---|---|---|
| 1 | A | deionized water | 85.60 |
| 2 | A | Merquat 100 | 2.00 |
| 3 | B | ppg-15 stearyl ether | 4.00 |
| 4 | B | steareth-21 | 0.60 |
| 5 | B | steareth-2 | 2.60 |
| 6 | C | triclosan | 1.00 |
| 7 | C | peg 8 | 4.00 |
| 8 | D | preservative | 0.20 |
|  |  | q.s. | 100.00 |

In separate vessels, the ingredients of phases A and B were heated to 75° C. With agitation, phase B was added to phase A, cooled to 60° C. and phase C ingredients were added. Agitation was continued and the reaction mixture was cooled and phase D ingredient added.

EXAMPLE 5

Cream Deodorant

| NO. | PHASE | INGREDIENT | % BY WEIGHT |
|---|---|---|---|
| 1 | A | deionized water | 36.00 |
| 2 | A | sorbitol | 3.00 |
| 3 | A | Merquat 100 | 2.00 |
| 4 | B | cetyl alcohol | 4.00 |
| 5 | B | glycerol stearate and peg 100 stearate | 10.00 |
| 6 | C | peg 8 | 4.00 |
| 7 | C | triclosan | 1.00 |
| 8 | D | aluminum zirconium complex, preservative | 40.00 |
|  |  | q.s. | 100.00 |

In separate vessels, the ingredients of phases A and B were heated to 75° C. With agitation, phase B was added to phase A, cooled to 60° C. and phase C ingredients were added. Agitation was continued thereby cooling the reaction mixture and phase D ingredients were added.

EXAMPLE 6

Roll-on Deodorant

| NO. | PHASE | INGREDIENT | % BY WEIGHT |
|---|---|---|---|
| 1 | A | deionized water | 77.00 |
| 2 | A | Merquat S | 3.00 |
| 3 | B | glyceryl stearate and peg 100 stearate | 10.00 |
| 4 | B | cetyl esters | 5.00 |
| 5 | C | triclosan | 1.00 |
| 6 | C | peg 8 | 4.00 |
|  |  | preservative q.s. | 100.00 |

In separate vessels, the ingredients of phase A and B were heated to 75° C. With agitation, phase B was added to phase A, cooled to 60° C. and phase C ingredients added. Agitation was continued thereby cooling the reaction mixture and phase D ingredients were added.

EXAMPLE 7

Roll-on Deodorant

| NO. | PHASE | INGREDIENT | % BY WEIGHT |
|---|---|---|---|
| 1 | A | deionized water | 84.60 |
| 2 | A | Merquat 100 | 2.00 |
| 3 | B | peg-15 stearyl ether | 4.00 |
| 4 | B | steareth 21 | 0.60 |
| 5 | B | steareth 2 | 2.60 |
| 6 | C | triclosan | 1.00 |
| 7 | C | peg 8 | 4.00 |
| 8 | D | triclocarbon | 1.00 |
| 9 | E | preservative, fragrance and dye |  |
|  |  | q.s. | 100.00 |

In separate vessels, the ingredients of phase A and phase B were heated to 75° C. With continued agitation phase B was added to phase A. Agitation was maintained and the reaction mixture cooled to 60° C. while adding phases D and E successively. The reaction mixture was cooled to 25° C.

What is claimed is:

1. A method of treating body odor which comprises applying to skin a composition comprising 0.01 to 5%, based on total composition weight, of an antimicrobial agent selected from the group consisting of trichlocarban (3, 4, 4'-trichloro carbanilide), triclosan (2, 4, 4'-trichloro-2'-hydroxy diphenyl ether), benzalkonium chloride, zinc phenosulfonate and zinc ricinoleate, 0.01 to 12%, based on total composition weight, of a cationic polymer selected from the group consisting of homopolymers of dimethyldiallyl ammonium chloride having an intrinsic viscosity of 0.1 to 2.5 and copolymers of dimethldiallyl ammonium chloride and acrylamide having an intrinsic viscosity of about 4.0 which contain about 10% to about 75%, by weight, dimethyldiallyl ammonium chloride and about 25% to about 90%, by weight, acrylamide, and the balance water.

2. The method of claim 1, wherein said polymer is a homopolymer of dimethyldiallyl ammonium chloride.

3. The method of claim 1 wherein said polymer is a copolymer of dimethyldiallyl ammonium chloride and acrylamide.

4. The method of claim 1, further comprising an antiperspirant agent.

5. The method of claim 4, wherein said antiperspirant agent is selected from the group consisting of aluminium zirconium complex, aluminum chlorohydrate and aluminum chlorohydrex P.G.

* * * * *